United States Patent
Gerrity (10) Patent No.: US 6,650,251 B2
(45) Date of Patent: Nov. 18, 2003

(54) SENSORY MONITOR WITH EMBEDDED MESSAGING ELEMENT

(76) Inventor: Dan Gerrity, 105 Duane St., Apt. 45B, New York, NY (US) 10007

( * ) Notice: Subject to any disclaimer, the term of this patent is extended or adjusted under 35 U.S.C. 154(b) by 0 days.

(21) Appl. No.: 10/085,741

(22) Filed: Feb. 28, 2002

(65) Prior Publication Data

US 2003/0160700 A1 Aug. 28, 2003

(51) Int. Cl.[7] ............................................. G08B 23/00
(52) U.S. Cl. ..................... 340/963; 340/425.5; 434/236; 600/558
(58) Field of Search ................................. 340/963, 961, 340/435, 901, 425.5, 945; 345/7; 348/563; 434/236, 29, 30, 35, 36, 49, 157; 600/558, 559

(56) References Cited

U.S. PATENT DOCUMENTS

| | | | |
|---|---|---|---|
| 3,060,795 A | 10/1962 | Corrigan et al. | ......... 434/236 X |
| 3,574,283 A | 4/1971 | Albers | ..................... 340/980 X |
| 4,395,600 A | * 7/1983 | Lundy et al. | ............... 381/73.1 |
| 5,027,208 A | 6/1991 | Dwyer, Jr. et al. | ......... 358/148 |
| 5,219,322 A | * 6/1993 | Weathers | ................. 434/238 X |
| 5,221,682 A | 6/1993 | Faris | ........................... 358/183 |
| 5,911,581 A | 6/1999 | Reynolds et al. | ........... 434/236 |
| 6,155,834 A | 12/2000 | New, III | ..................... 434/118 |
| 2002/0011925 A1 | 1/2002 | Hahn | ....................... 340/425.5 |

FOREIGN PATENT DOCUMENTS

DE 19952506 6/2001

OTHER PUBLICATIONS

Moshe Bar et al. 'Subliminal Visual Priming' Nov. 1998, Psychological Science, vol. 9, No. 6, pp. 464–469.
Endel Tulving et al. 'Priming abd Human Memory Systems' Jan. 19, 1990; Science vol. 247; pp. 301–305.
Caroyln Baker Cave 'Very Long–Lasting Priming in Picture Naming' Jul. 1997, Psychological Science, Vo. 8, No. 4, pp. 322–325.

* cited by examiner

Primary Examiner—Thomas J Mullen, Jr.
(74) Attorney, Agent, or Firm—Davidson, Davidson & Kappel, LLC (57) ABSTRACT

A system for measuring human perception at edges of awareness includes a message transmitter providing embedded messages embedded in supraliminal information, a sensory monitor for measuring reaction in an individual to the embedded messages, and a control system connected to the message transmitter, the control system receiving an input from the sensory monitor, the control system including a real-time feedback control loop altering a perceptability of the embedded messages with respect to the supraliminal messages as a function of the sensory monitor input.

21 Claims, 5 Drawing Sheets

SENSORY MONITOR WITH EMBEDDED MESSAGING ELEMENT

BACKGROUND OF THE INVENTION

The present invention relates to embedded messages that create a response in a viewer, and more particularly to a method and device for producing such messages, determining if such messages are effective, and tailoring such messages to individual responses.

U.S. Pat. No. 5,027,208 describes a therapeutic subliminal imaging system wherein a selected subliminal message is synchronized with and added to an existing video signal containing a supraliminal message. The combined preexisting supraliminal messages can be displayed on a video screen. The desired subliminal message is provided by a preprogrammed chip that is inserted by the user into a compact video processing circuit that combines the two signals for viewing. The video processing system of the invention synchronizes the video signal containing the supraliminal message with a signal containing the desired subliminal message. The system then either lightens or darkens portions of the supraliminal message, in a manner that is not consciously perceptible to the viewer, to present the subliminal message.

U.S. Pat. No. 5,221,962 discloses a method and apparatus for presenting subliminal messages that allow a user to verify the content and presence of the message, and adjust the message obviousness. A VCR overlays the television signals, and the user can turn a video control to reduce the amount of attenuation and the obviousness of the overlaid images until the images become imperceptible, and thus subliminal.

U.S. Pat. No. 6,155,834 discloses a system to teach a student to instantly recognize words without having to sound them out or go through other processes such as explaining the definition of the word. The words however are not embedded and are displayed to the student for conscious recognition. A computer systematically and continuously adjusts the requirements for word perception and recognition based on characteristics and ongoing responses of the individual student in a way that increases the speed and accuracy of word recognition.

U.S. Pat. Nos. 5,027,208, 5,221,962 and 6,155,834 cited above are herein incorporated by reference herein.

As demonstrated by tachistoscopic experiments, sensory inputs are first registered outside of conscious recognition, i.e. in the subconscious. Tachistoscopic systems may be designed to alter the dwell time of rapidly flashing images, for example. The images, as the dwell time increases, or, as the contrast increases or signal attenuation decreases, eventually enter the consciousness of the viewer.

However, many messages provided by these systems are generally designed to communicate subconsciously, and, if effective at all, are not tailored to individual responses.

SUMMARY OF THE PRESENT INVENTION

An object of the present invention is to permit creation of embedded messages that create a response in a viewer.

Another alternate or additional object of the present invention is to permit automatic tailoring of embedded messages to individuals.

The present invention provides a system for measuring human perception at edges of awareness comprising:

a message transmitter providing embedded messages embedded in supraliminal information;

a sensory monitor for measuring reaction in an individual to the embedded messages; and a control system connected to the message transmitter, the control system receiving an input from the sensory monitor, the control system including a real-time feedback control loop altering a perceptibility of the embedded messages with respect to the supraliminal messages as a function of the sensory monitor input.

Also provided is a method for providing embedded messages embedded in supraliminal messages comprising the steps of:

providing embedded messages with supraliminal information;

measuring a reaction in an individual to the embedded messages; and automatically controlling the embedded messages as a function of the reaction using a feedback loop, the feedback loop altering a perceptibility of the embedded messages with respect to the supraliminal messages as a function of the reaction.

The system and method of the present invention can monitor human awareness both below and above the liminal threshold of sensory awareness. Monitoring of sensory awareness is performed by a software component operating on a real-time operating system coupled to a sensor array. The sensor array collects data from sensors monitoring user reaction, or a user response, to images (or other sensory data) presented to the user. The sensory data presented to the user is presented at or near the boundary between conscious and subconscious sensory recognition.

Monitoring of user reception reaction allows the system to gauge efficacy of the sensory data in generating a response. Messaging elements are initially generated with physical characteristics registered below the threshold of conscious awareness, thereby broadening possibilities for communicating information or messages, for example by embedding them in other images or on a visual field.

Real-time feedback monitoring provides the basis for dynamically altering the physical characteristics of messaging elements as a function of user response as determined by the sensory monitor.

Messaging elements are, therefore, dynamically altered as a function of continuous monitoring of individual sensory recognition.

The system may be designed to continuously alter the physical characteristics of the messaging elements, and measure their impact, as a means of regulating the system to user-specific sensitivities. Messaging elements are varied using physical variables forming the boundaries between conscious and subconscious sensory awareness, such as alteration of duration, frequency, movement and non-time dependent variables such as color, contrast and pattern masking of the messaging elements. The system thus is dynamically tuned to user-specific sensory sensitivities both below the liminal threshold, and, if required, above the liminal threshold, to ensure that the user is responding to the messaging elements.

The dynamically and continuously constructed messaging elements are embedded within a sensory field of the user, such as a HUD or CRT display, or a visual field such as a windshield of an airplane. The embedded messaging elements may range from simple pictorial examples with literal meaning to complex patterns forming symbolic registers with latent, or metaphorical, meaning. Applications for the integrated system include medical diagnostic tools, warning systems for machine or process operators and training tools.

The present invention thus provides for dynamic control and placement of embedded messages by altering the physical characteristics of the embedded messages, or by altering the surrounding environment in which the messages are embedded, as a function of computer-based real-time monitoring of individual responses.

The embedded messages may include complex symbolic registers that provide complex meaning in the form of visual patterns, for example a skull and crossbones for poison.

The system thus also measures human perception at the edges of awareness through the real-time computer-based control loop by measuring, and monitoring user reactions to, or reception of, message elements presented beneath and beyond the threshold of physiologically based sensory awareness. Since each individual will likely have a different liminal threshold, real-time monitoring of the reaction or impact of the messaging elements provides the basis and functionality for measuring individual reception to the embedded messages and to dynamically alter for each individual the embedded messaging elements with respect to the variables forming the threshold of sensory awareness, such as duration, frequency, movement and non-time dependent variables such as color, contrast and pattern masking.

Whereas the sensory monitor measures sensory recognition about the liminal boundaries of an individual, a control application dynamically alters the messaging elements as a function of this monitoring of individual reception to accommodate individual physiology-based sensory sensitivities. As the system performs trial and error image manipulations seeking the desired response, the system collects data in the local database thereby learning individual sensory sensitivities and the mechanism for influencing individual users.

Having a real-time operating system, the sensory monitor provides deterministic monitoring and measurement within the millisecond range; having real-time monitoring of the efficacy of the embedded messaging elements presented to the subconscious regions of perception, the system provides for dynamic adaptation of messaging elements as a function of individual sensory abilities as monitored with useful purpose. In their simplest form, these embedded symbols include pictorial representations; in their complex form, they represent symbolic registers carrying latent, or metaphorical meaning. For example, symbolic registers could be presented as patterns within written text by dynamically altering the horizontal and vertical character spacing or by altering contrast about a pattern thereby embedding the symbolic register into the text. Presented below the liminal boundary of sensory awareness, symbolic registers expand the region of sensory awareness to include the gradient regions about the liminal threshold.

As described herein, applications include: (1) implementation as a medical diagnostic tool for detecting physiological changes impacting sensory pathways and processes as manifest in subconscious abilities such as perception about the edges of awareness; (2) dynamic generation and presentation of warning symbols for placement at the edges of conscious awareness as a function of the real-time monitoring of individual response; and (3) integration with training materials as a tool for reinforcing central points or developing unthought-of tendencies or second natures.

Knowing that conscious and subconscious mental abilities remain separated psychologically by physical constraints forming physiologically based gradients, introducing messaging elements to the subconscious area broadens areas of mental engagement to a particular task. Recognizing that brain and sensory physiology form the underpinnings of perception abilities, and that individual physiologies vary to measurable degrees with respect to sensory abilities, the present invention provides for dynamic adaptation to individual sensory abilities both conscious and subconscious.

For example, optical receptor and associated pathway neurology determine individual sensitivity and abilities with respect to visual perception. The individual ratio of optical rods to cones, therefore, determines the individual and specific ability to differentiate between colors and detect movement. Adjusting to an individual with a disproportionate number of optical rods, the system can increase a color variation, and then introduce movement of the image if color variation fails to register.

As a diagnostic tool, the embedded messaging elements measure individual sensory abilities at the edges of awareness against statistical norms as a method of detecting abnormalities within the sensory pathways as physiological abnormalities manifest in sensory abilities. Most sensory sensitivities reside within a narrow band of possibilities, and sensory pathways span from sensor to brain and, within the brain, outwardly from subconscious to conscious processing centers. Therefore, early detection of physiology based changes in sensory abilities is accomplished by monitoring individual ability in detecting the embedded messaging elements presented at the statistical norm of sensory awareness. As such, the present invention provides a noninvasive means of detecting physiological changes within the brain and outward sensory pathways beyond the range of imaging tools (such as MRI and PET scans) by detecting the manifestation of physiological changes as they affect perception about the regions of conscious awareness, rather than detecting physical changes underlying the mental abnormalities.

As a warning system, the system presents embedded messaging elements positioned within the gradient between conscious and subconscious sensory awareness to machine or control interfaces to prompt operators toward reaction to conditions while minimizing distractions thereby broadening the possibilities of perception. Moreover, the embedded messaging elements system together with the sensory monitor allows for dynamic altering of the physical characteristics of the messaging elements (to measure the liminal threshold and alter messaging element characteristics as a function of individual sensory sensitivities or lack thereof) as a function of perception as measured through reaction. Presenting the embedded messaging elements to the regions of perception outside of consciousness allows the operator to continue concentrating on the task at hand while incorporating additional information. By way of example, if the machinery were a combat aircraft, and the intended warning an indication of possible missile threat, the embedded messaging elements might include pictorial representations such as missile indications or suggestion for evasive maneuvers. In this example, the embedded messaging elements provide a warning system without distracting the pilot from flying the aircraft. Thus, the system broadens the region of awareness to include the boundary regions, or gradient areas between conscious and subconscious recognition (as defined through individual physiologically-based constraints).

Recognizing the physiological foundations of perception, variables within individuals physiologically will alter individual sensory abilities and sensitivities,; the sensory monitor measures these variations through the real-time feedback-based deterministic control loop, whereas the embedded messaging elements alter the embedded message position with respect to gradient variables as a function of individual reaction in pursuit of the desired, or targeted, response. Furthering the combat aircraft example, if the pilot fails to acknowledge these embedded messaging signals, as recognized through the monitoring of reaction or trajectory toward a desired reaction (as measured through the sensing of accelerations or change in accelerations the aircraft is subject to or a controller movement), the system alters the embedded message position with respect to duration, frequency, movement and/or non-time dependent variables such as color, contrast and pattern masking toward the region of consciousness until such time that positive reception is indicated.

As a warning system, the system is applicable to any operative situation such as automobile, aircraft, spacecraft or process control operating device. Overall, the system merges human and machine control by providing a degree of machine-based control over the operator. Presenting messages, or instructions, below and about the liminal threshold of sensory awareness, the system provides for the broadening and deepening of user and machine interface. Having a local database to collect data for analysis, together with the ability for trial and error image representations for intended response, allows the system to independently learn the mechanisms to control individual operators and the degree of control possible.

As a training tool, such as adopted to Army training routines, where key points are typically learned through repetition or where a second nature is desired, the system provides a means of reinforcing central points or developing a second nature by presenting elements to the subconscious where primary behaviors are seated. In the case where training materials are presented to the reader on a computer monitor, in addition to simple embedded messaging elements, more complex messaging are possible thereby extending the possibilities for broadening, deepening, reinforcing or negating interpreted meanings. For example, introducing patterns within the text displayed on a CRT provides the possibilities to alter the interpreted meaning of the written message through the introduction of an embedded message linked to a symbolic register of specific meaning. These patterns are then embedded within the written text by dynamically altering horizontal and vertical line and character spacing, or by varying gradient variables such as text-character contrast or color, such that the pattern is presented to the subconscious region of perception.

Functioning as symbolic registers, the embedded messaging elements may carry latent meaning in the form of complex patterns forming visually presented metaphors. As depicted in the above training example, the system allows for the introduction of patterns in response to an individual ability to absorb materials or reverse previously learned tendencies. For example, if a training subject has previously, but incorrectly learned, that certain compounds are nonvolatile under exposure to sunlight, then, depending upon the response to questions, the systems would introduce symbolic registers into the training materials (such as universally understood representations for danger and daylight) in combination to reinforce or negate interpretation. For example, the intended association may be accomplished by linking danger and sunlight in combination to the written word through the introduction of embedded messaging elements, which negate, or otherwise alter, previous interpretations.

A library of symbolic registers arranged in classes and class members such that these symbolic registers have known functions when linked to, or embedded within, text messaging are possible. Combining these symbolic registers with literal messages, the sensory monitor may gauge the impact of these embedded symbolic registers on interpretation. As such, the symbolic registers serve as a language analogous to the use of music to augment visuals. Where the chords form melodies that invoke specific moods or meanings, which color interpretation of the visuals, the symbolic registers interplay with written words to alter interpretation.

As the system catalogs symbolic registers into classes and class members for specific purposes, the system may learn both the universality of symbol interpretation in addition to a cultural specific symbolic register vernacular. For example, that which is universally understood to convey sorrow might have more specific, and deeper, meaning within a narrower culture context. "Embedded messages" as defined herein are messages designed to be just at or near the liminal boundary of perception.

BRIEF DESCRIPTION OF THE DRAWINGS

A preferred embodiment of the present invention is described below by reference to the following drawings, in which.

DETAILED DESCRIPTION

Figure 1:
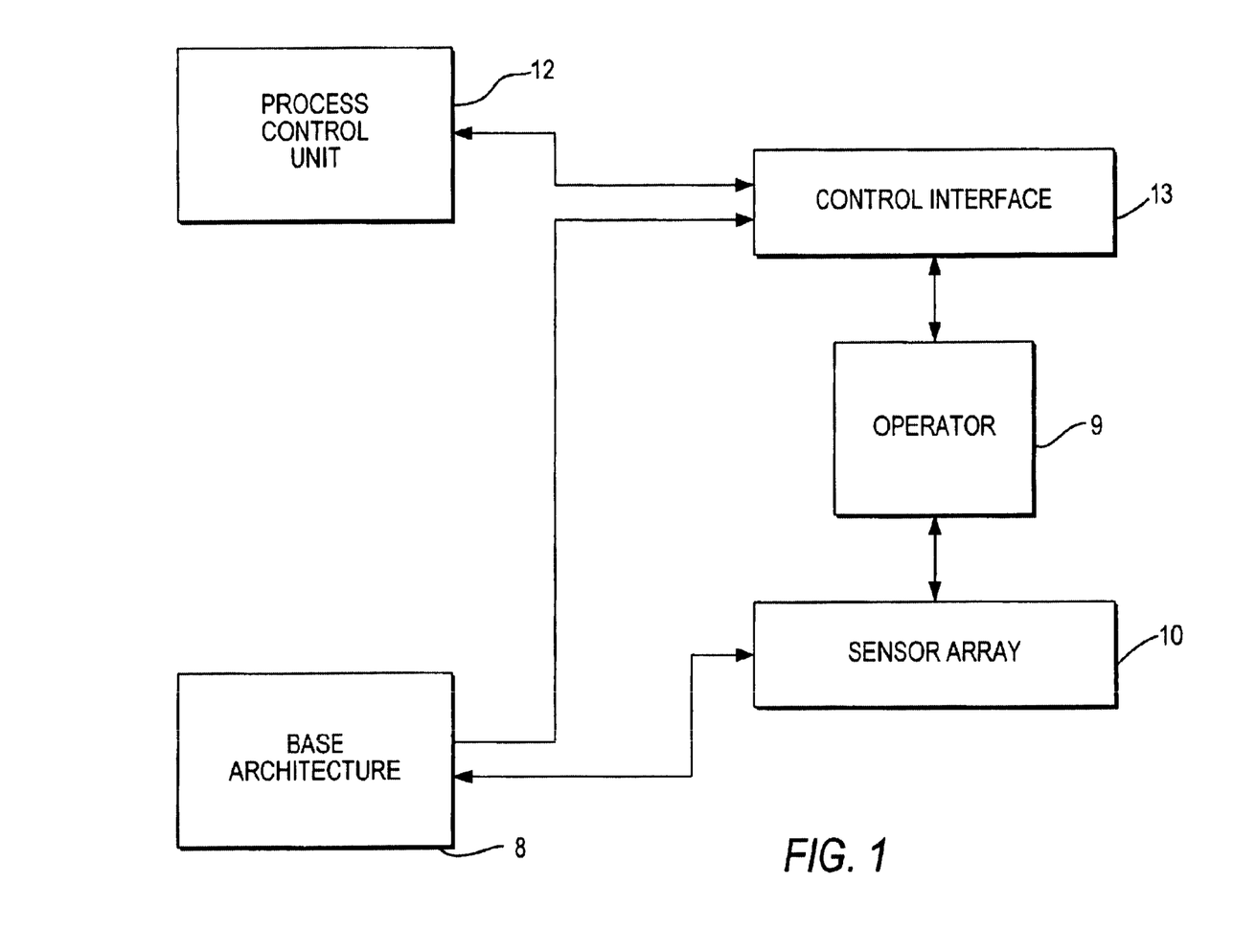
FIG. 1 shows a schematic representation of the base architecture of the present invention.

FIG. 1 shows a schematic representation of the system of the present invention for use as a warning system. An operator 9 is presented embedded messaging elements and a supraliminal message at a control interface or message provider 13, for example a CRT in an airplane showing infrared night vision information as the supraliminal message. The messaging elements may be embedded within the night vision information, and may be words, such as "TURN RIGHT" or "TURN LEFT" shown first at a level not perceptible to an average operator 9.

A sensor array 10, which may for instance include a vehicle direction sensor or automobile traction control sensor or direction controller angle sensor, can read reaction from the operator. Thus a change in the controller and the direction of the change can be read by the sensor array 10.

Figure 2:
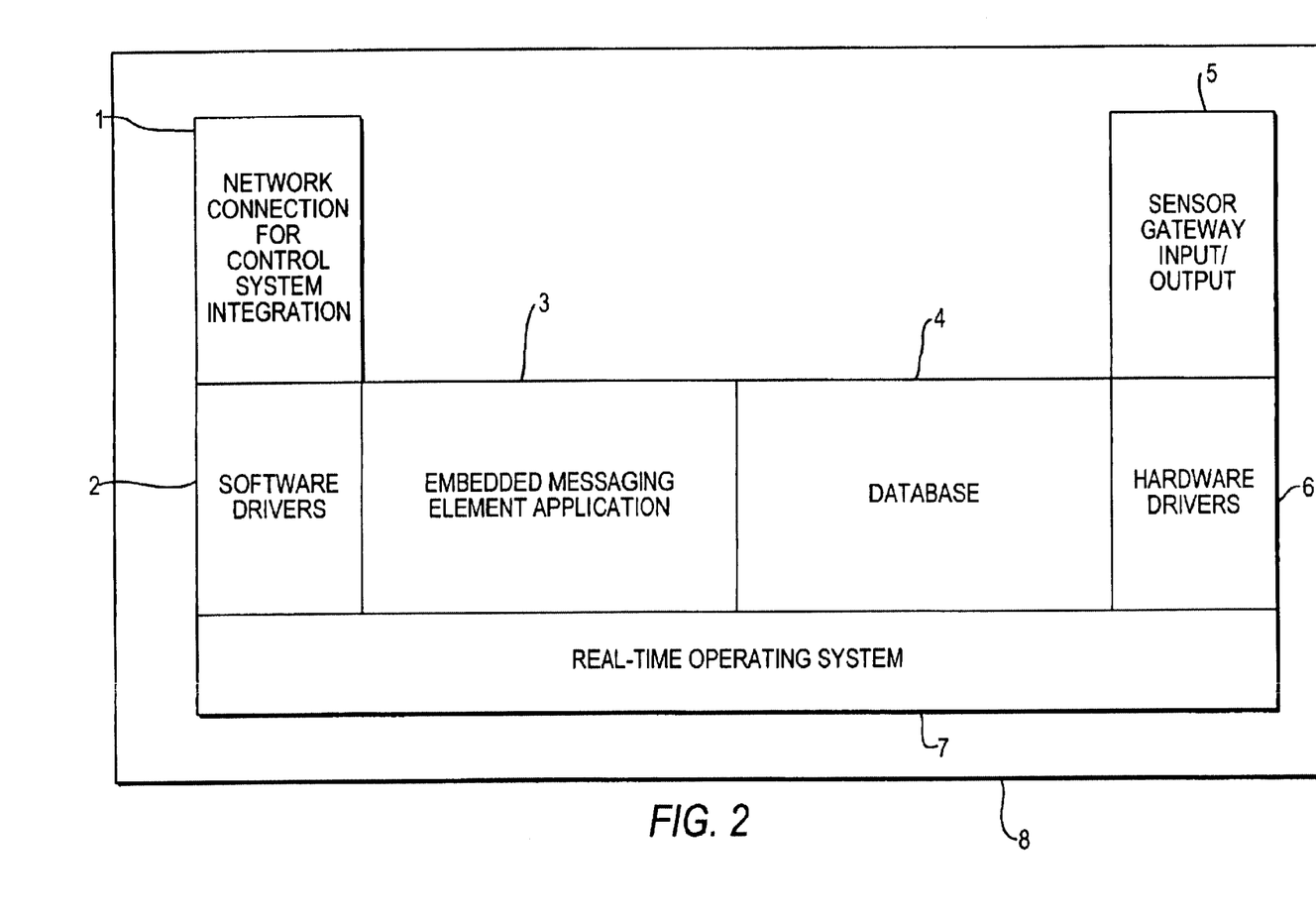
FIG. 2 shows schematically the embodiment of the present invention for use in a warning system.

The sensor array 10 provides an input to a system base architecture 8, which functions as a system control system, shown in FIG. 2. The reaction of operator 9 thus is received through the sensor array 10 and the data is further processed and analyzed by the base architecture 8, which is connected to the sensor array via an I/O device 5. A hardware driver 6 can convert signals from the sensor array 10 into digital signals capable of being read by a real time operating system (RTOS), for example VXWORKS, by Wind River Corporation of Alameda, Calif. Software run on the RTOS can determine the signals from the sensor array indicating a response, or lack of responses, as a function of input (message presentation of sensory gradient values) at a point in time. For example if the controller angle changes more than 30 degrees to the left, a left turn is recognized, and if the controller angle changes more than 30 degrees to the right, a right turn is recognized. However, the reaction of the individual may includes any predetermined hand eye, foot or body weighting movement or a vocalization. This positive indication is, therefore deterministically accounted for as a result of the embedded message of specific characteristics. Through this closed loop process, the system learns the specific receptivity and sensitivities of individual operators.

A process control unit 12 determines if a warning is necessary, and may be connected to both the base architecture 8 though a network connection 1, and to the control interface 13. The network connection 1 may be for example an Ethernet card, provides the base architecture 8 with a connection to a network and the process control unit 12, for example a LAN.

Process control unit 12 for example may be an infrared device for determining a stationary object in the path and at the sides of the airplane, for example at a range of 1000 meters.

A software driver 2 can read the Ethernet messages, strip them of any headers, and pass the relevant information to an embedded message element application 3. The embedded message application 3 can determine, for example, that a stationary or approaching object is in the path of the vehicle and also to the right of the vehicle, based on the input from process control unit 12.

The message application 3 then can begin flashing a proper embedded message at, for example, a predetermined intensity. For example, "TURN LEFT" is flashed on control interface 13, embedded in the supraliminal night vision information.

If the pilot fails to respond in a predetermined time frame, the intensity of the embedded message can, for example, be increased slightly (or the surrounding intensity of the night vision screen information decreased) until a response is registered by the determination that from the sensors that the controller has been moved to the left.

If the pilot responds immediately, the intensity, or activity, of future messages can be decreased a predetermined amount.

A database 4 can store the intensity at which the pilot responded, and use this intensity as the predetermined intensity in later applications.

If an immediate response is registered the next time an embedded message is shown, the intensity can be lowered for the next embedded message.

The base architecture 8 may be a computer or other logic unit, which can include for example a processor commercially-available from the Intel Corporation.

The system thus can perform trial and error image manipulations seeking the desired response, and the system collects data for analysis in the embedded database 4 thereby learning individual sensory sensitivities and the mechanism for influencing individual users.

Moreover, the present invention can compensate for varying individual conditions, for example as the pilot becomes sleepier during a flight, the messages can be automatically intensified.

The real-time operating system 7, for example VXWORKS, commercially-available from the Wind River Corporation, provides the sensory monitor with deterministic monitoring and measurement within the millisecond range.

Figure 3:
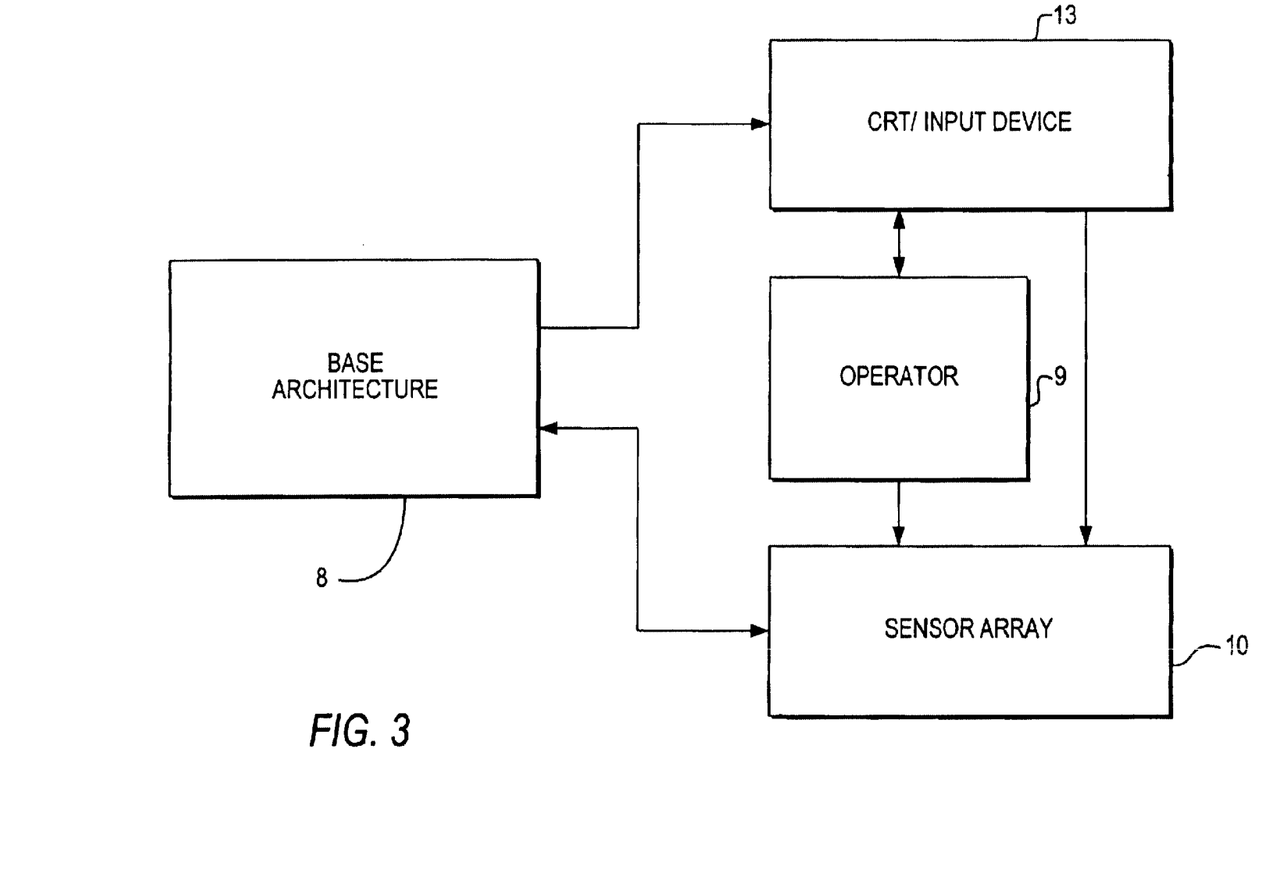
FIG. 3 shows schematically the embodiment of the present invention for use as a training tool or diagnostic tool.

FIG. 3 shows a schematic representation of the present invention for use as a training or diagnostic tool. When the present invention is used as a training tool for training routines, embedded training messages are presented to the operator 9 on a CRT, or television, with input device 13. The training messages may be for example pictorial representation of foreign language words. The sensor array 10, which can be a computer that queries the operator to choose the proper meaning of a foreign language word, receives the reaction of operator 9 and then communicates the results with the base architecture 8, as in FIG. 2.

When used as a diagnostic tool, the system measures individual sensory abilities at the edges of awareness against statistical norms as a method of detecting abnormalities within the sensory pathways as physiology abnormalities manifest in sensory abilities. The present invention provides a noninvasive means of detecting physiological changes within the brain of the operator 9 and outward sensory pathways by detecting the manifestation of physiological changes as they affect perception. When the present invention is used as a diagnostic tool, embedded messages are displayed to the operator 9 on a CRT with input device 13. The sensor array 10 receives the operator's 9 reactions and communicates the results with the base architecture 8.

For example, the same training technique for foreign language meaning can be used to determine a problem in the brain of an operator for learning foreign language words, as measured against statistical norms.

Supraliminal messages as defined herein can include those provided by a normal visual field of an individual, for example through a windshield of a vehicle.

Figure 4:
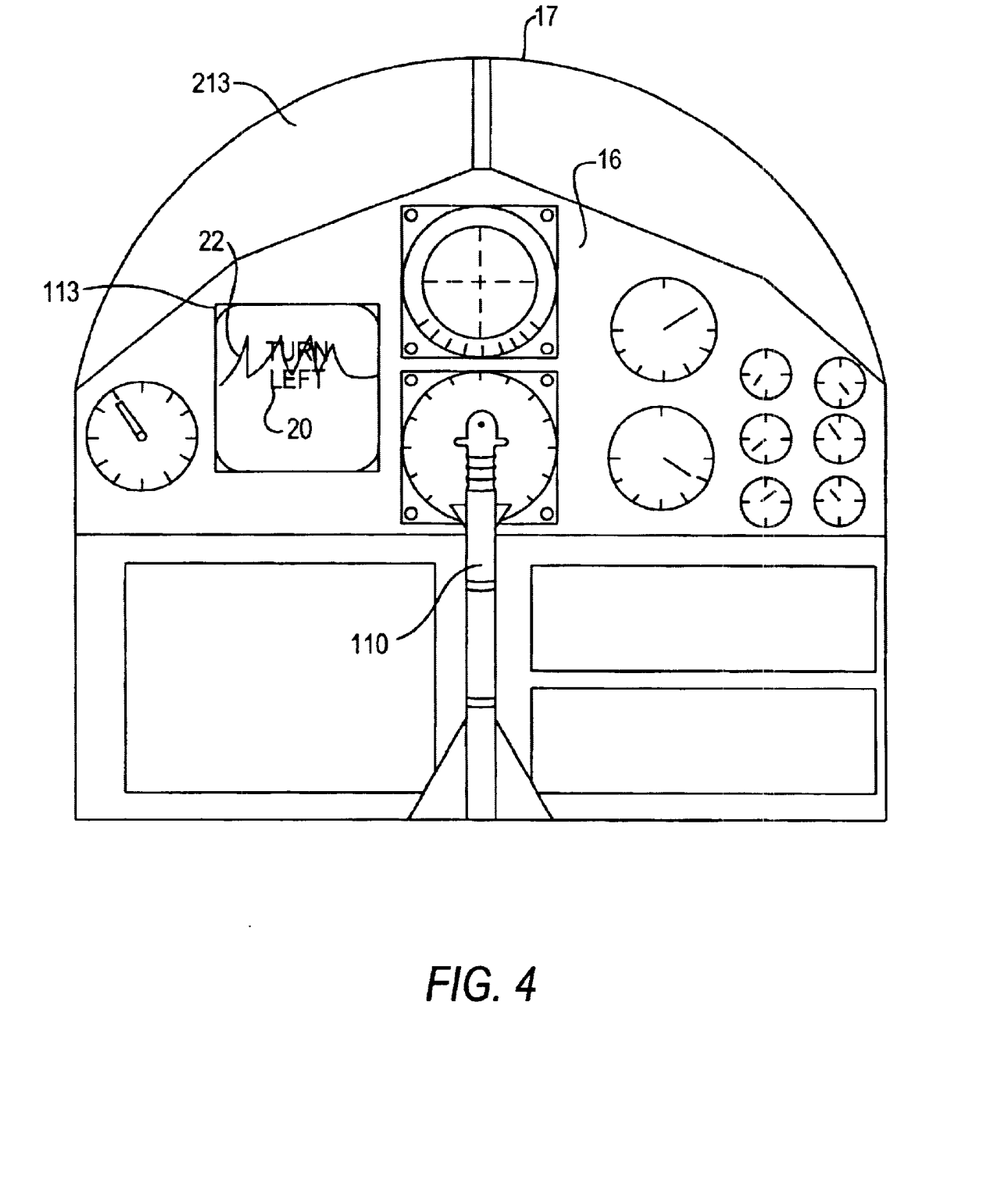
FIG. 4 shows a specific embodiment of the present system for use in a jet fighter.

FIG. 4 shows a schematic representation of the present invention for a warning system in a combat aircraft. The warning system provides embedded messages 20 (shown for clarity) embedded in supraliminal messages 22 to the pilot. The warning system in a combat aircraft increases the awareness level of the pilot without distracting the pilot from flying the aircraft. The warning system utilizes a screen 113 as a message transmitter for embedded supraliminal messages 20 to the pilot, while operating the aircraft. The display screen 113 is integrated into the instrument panel 16 of the cockpit 17. Pilot reactions can be monitored through an aircraft controller 110 (See FIG. 5 as well).

Figure 5:
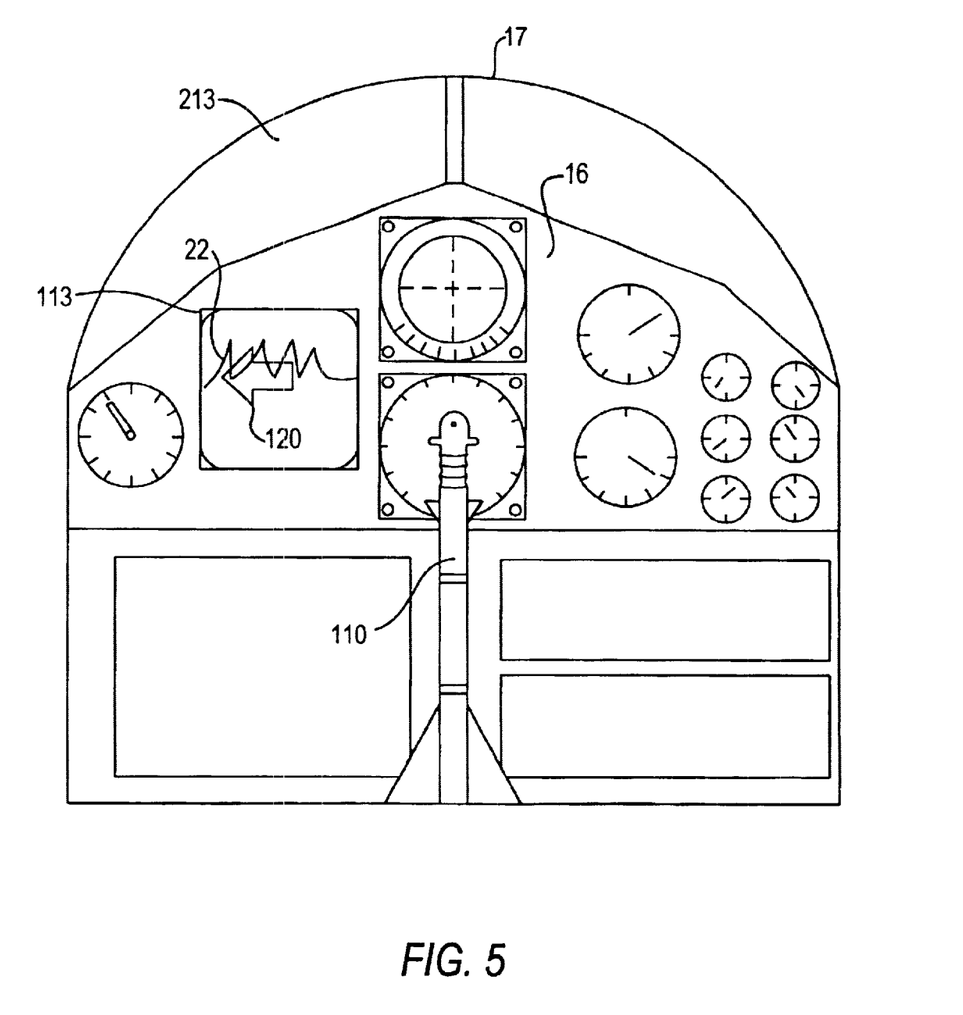
FIG. 5 shows the embodiment of FIG. 4 with a symbolic messaging element.

Alternately, as shown in FIG. 5, the embedded messages may include a symbol, for example arrow 120, of varying intensity. The arrow 120 also can be moved from the inner regions of the display screen 113 toward the peripheral region of screen 113 (i.e. to the left in FIG. 5), as well as having the intensity varied. Thus two gradient variables (intensity and movement) are simultaneously used to alter perceptibility of the embedded message.

Alternately, the embedded messages 20 could be directly shown on the windshield 213 of the cockpit.

What is claimed is:

1. A system for measuring human perception at edges of awareness comprising:
   a message transmitter providing embedded messages embedded in supraliminal information;
   a sensory monitor for measuring reaction in an individual to the embedded messages; and
   a control system connected to the message transmitter, the control system receiving an input from the sensory monitor, the control system including a real-time feedback control loop altering a perceptibility of the embedded messages with respect to the supraliminal messages as a function of the sensory monitor input.

2. The system as recited in claim 1 wherein the embedded messages and supraliminal messages are visual images.

3. The system as recited in claim 1 wherein the perceptibility is controlled by altering at least one of duration, frequency, movement, intensity, color and contrast of the embedded messages.

4. The system as recited in claim 1 wherein the perceptibility is controlled by altering at least one of an intensity, color and contrast of the supraliminal message.

5. The system as recited in claim 1 wherein the reaction of the individual is a predetermined input to the control system.

6. The system as recited in claim 5 wherein the reaction of the individual includes at least one predetermined hand, eye, foot or body weighting movement or a vocalization.

7. The system as recited in claim 1 wherein the reaction occurs within a predetermined time period.

8. The system as recited in claim 1 wherein the feedback control loop has a setpoint corresponding to a predetermined reaction.

9. The system as recited in claim 1 further comprising a database of statistical norms for measurement of the perceptibility at predetermined levels.

10. The system as recited in claim 9 wherein the system is a medical diagnostic tool, and the reaction relates to a specific medical abnormality.

11. The system as recited in claim 1 wherein the system is a warning system for the individual, the embedded messages disclosing a warning, the reaction indicating acknowledgment of the warning.

12. The system as recited in claim 1 wherein the embedded messages are chosen from a predetermined library of symbols.

13. The system as recited in claim 1 wherein the message transmitter is a screen.

14. The system as recited in claim 1 wherein the sensory monitor includes an aircraft direction controller.

15. The system as recited in claim 1 wherein the sensory monitor includes an automobile traction system.

16. A method for providing embedded messages embedded in supraliminal messages comprising the steps of:

providing embedded messages with supraliminal information;

measuring a reaction in an individual to the embedded messages; and automatically controlling the embedded messages as a function of the reaction using a feedback loop, the feedback loop altering a perceptibility of the embedded messages with respect to the supraliminal messages as a function of the reaction.

17. The method as recited in claim 16 wherein the perceptibility is altered via at least one of duration, frequency, movement, intensity, color and contrast of the embedded messages.

18. The method as recited in claim 16 wherein the embedded messages are displayed within a field of vision of an individual.

19. The method as recited in claim 16 wherein the embedded messages disclose a warning, the reaction indicating acknowledgment of the warning.

20. The method as recited in claim 16 wherein the embedded messages are chosen from a predetermined library of symbols, the library including classes of meanings.

21. The method as recited in claim 16 further comprising selecting the embedded messages from a local database of stored messages, the stored messages being a function of previously measured perceptibility of specific users.

* * * * *